(12) United States Patent
Senko

(10) Patent No.: US 7,982,181 B1
(45) Date of Patent: Jul. 19, 2011

(54) METHODS FOR IDENTIFYING AN APEX FOR IMPROVED DATA-DEPENDENT ACQUISITION

(75) Inventor: Michael W. Senko, Sunnyvale, CA (US)

(73) Assignee: Thermo Finnigan LLC, San Jose, CA (US)

( * ) Notice: Subject to any disclaimer, the term of this patent is extended or adjusted under 35 U.S.C. 154(b) by 460 days.

(21) Appl. No.: 12/014,701

(22) Filed: Jan. 15, 2008

(51) Int. Cl.
   *B01D 59/44* (2006.01)
(52) U.S. Cl. .......... 250/282; 250/281; 250/283; 702/22; 702/23; 702/26; 702/27; 702/28
(58) Field of Classification Search .......... 250/281–300; 702/22, 23, 26, 1, 27, 28
   See application file for complete search history.

(56) References Cited

U.S. PATENT DOCUMENTS

| | | | | |
|---|---|---|---|---|
| 4,682,027 | A * | 7/1987 | Wells | 250/291 |
| 4,941,101 | A * | 7/1990 | Crilly | 702/32 |
| 5,107,109 | A | 4/1992 | Stafford, Jr. et al. | |
| 5,436,447 | A * | 7/1995 | Shew | 250/291 |
| 5,481,476 | A | 1/1996 | Windig | |
| 5,572,022 | A | 11/1996 | Schwartz et al. | |
| 5,672,869 | A * | 9/1997 | Windig et al. | 250/282 |
| 5,885,841 | A * | 3/1999 | Higgs et al. | 436/89 |
| 6,002,986 | A | 12/1999 | Mito | |
| 7,009,174 | B2 | 3/2006 | Le Blanc | |
| 7,223,965 | B2 * | 5/2007 | Davis | 250/282 |
| 7,279,679 | B2 * | 10/2007 | Old et al. | 250/282 |
| 7,297,941 | B2 | 11/2007 | Senko et al. | |
| 7,501,621 | B2 * | 3/2009 | Willis et al. | 250/287 |
| 7,519,488 | B2 * | 4/2009 | Fu et al. | 702/69 |
| 2004/0181351 | A1 * | 9/2004 | Thompson et al. | 702/76 |
| 2004/0191351 | A1 | 9/2004 | Kim et al. | |
| 2004/0195500 | A1 * | 10/2004 | Sachs et al. | 250/282 |
| 2004/0251409 | A1 * | 12/2004 | Le Blanc | 250/288 |
| 2005/0016276 | A1 * | 1/2005 | Guan et al. | 73/579 |
| 2005/0261838 | A1 * | 11/2005 | Andreev et al. | 702/22 |
| 2005/0288872 | A1 * | 12/2005 | Old et al. | 702/30 |
| 2006/0243900 | A1 * | 11/2006 | Overney et al. | 250/284 |
| 2006/0255258 | A1 * | 11/2006 | Wang et al. | 250/282 |
| 2006/0284067 | A1 * | 12/2006 | Senko et al. | 250/282 |
| 2006/0284069 | A1 * | 12/2006 | Le Blanc | 250/282 |
| 2007/0023633 | A1 * | 2/2007 | Wang et al. | 250/282 |
| 2008/0067346 | A1 * | 3/2008 | Amster et al. | 250/282 |
| 2008/0149821 | A1 * | 6/2008 | Senko | 250/282 |

OTHER PUBLICATIONS

Andreev et al., "A Universal Denoising and Peak Picking Algorithm for LC-MS Based on Matched Filtration in the Chromatographic Time Domain," Anal. Chem., vol. 75 (No. 22), p. 6314-6326, (2003).

(Continued)

*Primary Examiner* — Bernard E Souw
*Assistant Examiner* — Michael J Logie
(74) *Attorney, Agent, or Firm* — Michael C. Staggs

(57) ABSTRACT

A method of analyzing data from a mass spectrometer provides data-dependent acquisition. An extracted ion chromatogram (XIC) is created for each m/z data point of mass spectral scans and the XIC for each m/z data point are correlated to a model function to obtain a XIC correlation value. A weighting function is applied to the XIC correlation value to obtain a current weighted intensity for each m/z point, which is used to reconstruct a weighted mass spectrum. The value or range of intensities of interest of the weighted intensity data or raw data is transformed from the time domain into the frequency domain, and the transformed data is used to make a real-time decision for the data-dependent acquisition. The data-dependent acquisition can be the performance of tandem mass spectrometry. A sample processing apparatus receives the sample and a computer readable medium provides instructions to the apparatus.

25 Claims, 7 Drawing Sheets

OTHER PUBLICATIONS

Kohli et al., "An Alternative Sampling Algorithm for Use in Liquid Chromatography/Tandem Mass Spectrometry Experiments," Rapid Commun. Mass Spectrom, Wiley InterScience, p. 589-596, (2005).

Wenner et al, "Factors that Affect Ion Trap Data-Dependent MS/MS in Proteomics," J Am Soc Mass Spectrom, vol. 15, p. 150-157, (2004).

* cited by examiner

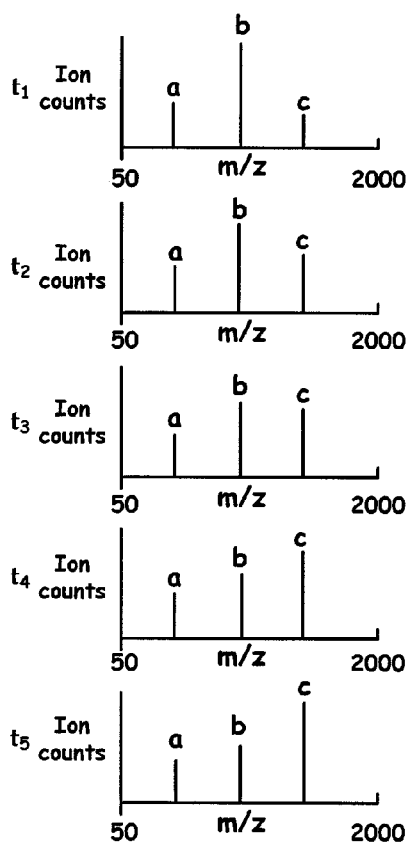
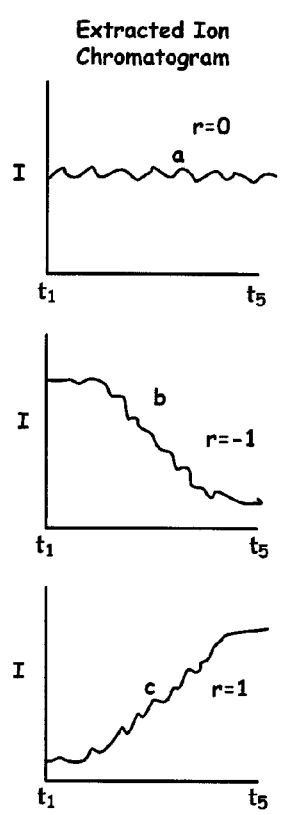
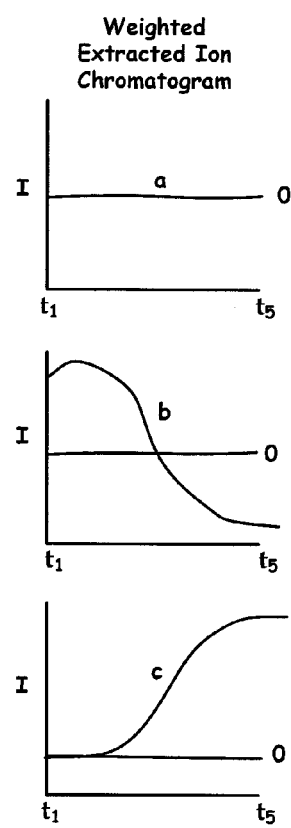
Fig. 3A     Fig. 3B     Fig. 3C
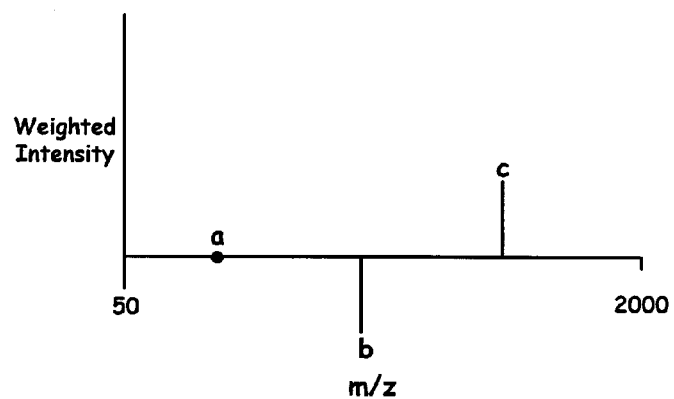
Fig. 3D

METHODS FOR IDENTIFYING AN APEX FOR IMPROVED DATA-DEPENDENT ACQUISITION

BACKGROUND OF THE INVENTION

1. Field of the Invention

The present invention relates to the field of data-dependent acquisition in a mass spectrometer, and more particularly to the field of tandem mass spectrometry.

2. Discussion of the Related Art

Mass spectrometers are often coupled with chromatography systems in order to identify and characterize eluting species from a test sample. In such a coupled system, the eluent is ionized and a series of mass spectral scans are obtained at specified time intervals for subsequent data analysis. As the test sample may contain many species or compounds, it is often desirable to be able to automatically determine or identify species or compounds of interest as they elute and perform tandem mass spectrometry analysis to characterize them.

Tandem mass spectrometry is a mode of operation that utilizes multiple stages of mass analysis with a collision or reaction process between each stage of mass analysis. The coupling of multiple stages of mass analysis provides the ability to determine or identify species or compounds of interest by providing additional information on the fragmentation or reaction characteristics of the compound. Tandem mass spectrometry having two stages of mass analysis is typically referred to as mass spectrometry/mass spectrometry (MS/MS). In data-dependent mode, the eluting sample is automatically selected for further analysis by MS/MS when the signal intensity of a mass spectral peak is above a user specified intensity. But, direct intensity-based triggering is far from ideal, for several reasons. First, high baselines will cause triggering at all masses. Second, tandem mass spectra will be collected as soon as an eluting chromatographic peak exceeds the threshold value, and not at the ideal point, which is at the top of the chromatographic peak where it is at its greatest intensity. Collecting a sample for MS/MS at the beginning of the elution of the chromatographic peak produces a lower quality spectrum, due to a limited number of sample ions being combined with a high percentage of background contaminants. For ion accumulating mass spectrometers, which use automatic gain control, such as quadrupole ion traps and Fourier transform mass spectrometers, performing MS/MS at the beginning of elution also requires the largest amount of time, thus slowing analysis. Third, direct intensity-based triggering results in redundant MS/MS acquisition of compounds during the entire elution time.

U.S. Pat. No. 7,009,174 describes a method of dynamic background signal exclusion in chromatography/mass spectrometry data-dependent data acquisition to detect species eluting at a low level of concentration that elute simultaneously with a number of other major components by identifying ions having a fast rising mass signal. The ions having the fastest rising mass signal may be identified by subtracting a previously acquired mass spectrum, or an average of previously acquired mass spectra, from the current mass spectrum. The disadvantage of taking a sample of the eluted ionized species at the fastest rising mass signal is that MS/MS can often be triggered on noise spikes in the spectrum, caused by either charged droplets from the ion source or electrical noise in the detection system.

SUMMARY OF THE INVENTION

Accordingly, the present invention provides a method of enabling data-dependent data acquisition in a mass spectrometer, including: obtaining a plurality of mass spectra from a sample; selecting from the plurality of mass spectra, a set of eluting m/z peaks of interest from a weighted mass spectrum by way of a correlation technique; obtaining phase data resulting from portions of extracted ion chromatographs (XIC) from the selected set of eluting m/z peaks of interests so that a subset of the set of eluting m/z peaks of interest can be identified; and triggering off of the identified subset of the eluting m/z peaks of interest based on the obtained phase data so that real-time data is acquired that corresponds to one or more desired eluting m/z peaks of interest.

Another aspect of the present invention includes a computer readable medium that provides instructions. When the instructions are executed on a processor, such instructions can cause the processor to perform a method of controlling a mass spectrometer that includes: obtaining a plurality of mass spectra from a sample; selecting from the plurality of mass spectra, a set of eluting m/z peaks of interest from a weighted mass spectrum by way of a correlation technique; obtaining phase data resulting from portions of extracted ion chromatographs (XIC) from the selected set of eluting m/z peaks of interests so that a subset of the set of eluting m/z peaks of interest can be identified; and triggering off of the identified subset of the eluting m/z peaks of interest based on the obtained phase data so that real-time data is acquired that corresponds to one or more desired eluting m/z peaks of interest.

In another aspect of the present invention, embodiments can include a sample processing apparatus for data-dependent acquisition. The apparatus may include a mass spectrometer, a system controller for controlling the mass spectrometer, and a machine-readable medium coupled to the system controller. The machine-readable medium may have a memory that stores a set of instructions that controls data-dependent acquisition by the mass spectrometer. The set of instructions may control parameters of the data-dependent acquisition of the mass spectrometer by obtaining a plurality of mass spectra from a sample; selecting from the plurality of mass spectra, a set of eluting m/z peaks of interest from a weighted mass spectrum by way of a correlation technique; obtaining phase data resulting from portions of extracted ion chromatographs (XIC) from the selected set of eluting m/z peaks of interests so that a subset of the set of eluting m/z peaks of interest can be identified; and triggering off of the identified subset of the eluting m/z peaks of interest based on the obtained phase data so that real-time data is acquired that corresponds to one or more eluting m/z peaks of interest.

Accordingly, the present invention is directed to data-dependent peak selection techniques and apparatus that enable the identification of eluting compounds in tandem mass spectrometer systems. Such methods and apparatus, as disclosed herein, are beneficial in applications, such as, but not limited to, in-vitro sample analysis, proteomics analysis and/or complex sample analysis wherein identification of desired eluting peaks requires optimal performance for identification.

BRIEF DESCRIPTION OF THE DRAWINGS

FIG. 3A illustrates an example of five mass spectra taken at different times.

FIG. 3B illustrates extracted ion chromatograms created for each of the m/z data points within measured mass spectra.

FIG. 3C illustrates weighted extracted ion chromatograms for the m/z data points obtained in FIG. 3A.

FIG. 3D illustrates a weighted mass spectrum based on XIC correlation values of the extracted ion chromatograms.

DETAILED DESCRIPTION

Figure 1A:
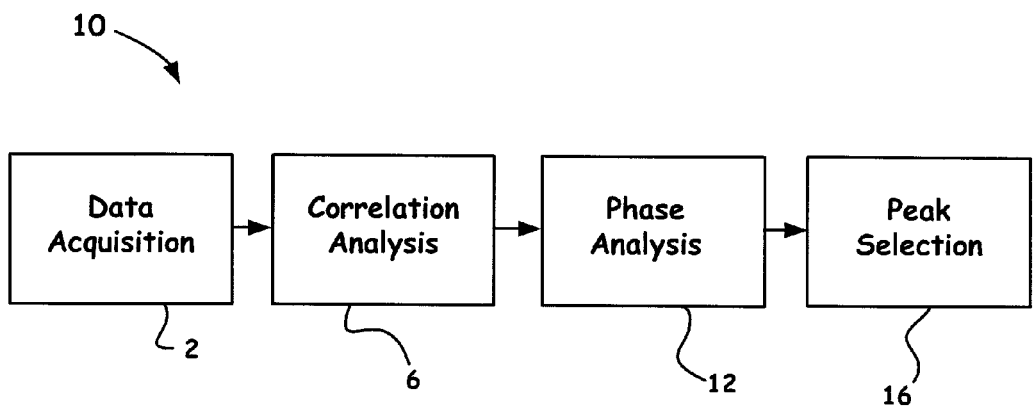
FIG. 1A is a block diagram of a combination method in accordance with embodiments of the present invention.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

Where data-dependent acquisition is encompassed within the performance of mass spectrometry, such as, successive stages of mass spectrometry, often tandem mass spectrometry, it is beneficial to perform mass spectrometry on a precursor ion near the apex of the chromatographic peak containing the precursor ion. In tandem mass spectrometry, for example, precursor ions are further fragmented by collision or reaction within a separate chamber or within the ion trap itself. The further fragmentation of the precursor ions on which mass spectra are obtained creates more information for the characterization or identification of compounds eluting from the chromatographic column. The apex of the chromatographic peak is an advantageous place to collect the precursor ions for tandem mass spectrometry because the flux of ions into the ion trap near the apex of the peak is at its greatest. Therefore, the ion trap may be quickly filled to capacity with the ions of interest, resulting in the faster production of mass spectra and improved signal to noise ratios. The signal to noise ratio may be enhanced because the time to fill the ion trap to capacity is minimized so that any contaminants, if present within the sample, may be present in insignificant quantities. Additionally, filling the ion trap to capacity is valuable because it provides more precursor ions within the resulting mass spectrum.

Accordingly, the present invention is generally directed to methods of determining when to make a data-dependent acquisition in real-time. In particular, the embodiments disclosed herein apply to the determination of when to execute tandem mass spectrometry on a precursor. As an unexpected result, combining the two methods of the present invention for data-dependent peak selection provides a superior performance in making such a determination in contradistinction to utilizing alone any of the methods discussed herein.

One of the methods, described herein as the "correlation" method, includes taking the data collected from a mass spectrometer and correlating the data to a model function. Such a similar method is described in U.S. Pat. No. 7,297,941, entitled, "Methods For Improved Data dependent Acquisition," to Senko et al., the disclosure of which is incorporated by reference in its entirety.

In particular, one compares an extracted pattern of separated substances, i.e., an ion chromatogram, to the front half of a peak, such as, for example, a model Gaussian peak. The observed abundance may then be multiplied by the correlation. In this way, masses that are initially eluting are unaffected, masses that constantly elute are multiplied by zero, and masses on the tail of the elution are multiplied by minus one. Such a method includes applying a weighting function to the correlated data to obtain a reconstructed weighted mass spectrum to make a real-time decision for a data-dependent acquisition. This weighting step helps emphasize masses of interest from constantly eluting chemical noise or background. In order to trigger near the top of the chromatographic peak, the correlation processing can be combined with a simple apex detection which looks for a decrease in the abundance at any mass in the chromatogram, but more often, as disclosed herein, it is desired to combine the correlation method with a second method (i.e., the phase method as disclosed in greater detail hereinafter) for a more accurate data-dependent determination of eluting m/z peaks of interest.

The second method, in particular, provides for improved data-dependent peak detection based upon analysis of extracted ion chromatograms that have been transformed from the time domain into the frequency domain. Such a similar method is described in Pending U.S. application Ser. No. 11/644,180, entitled, "Method And Apparatus For Identifying The Apex of A Chromatogram," to Senko, the disclosure of which is incorporated by reference in its entirety. While other data characteristics can be used as indicators, it has been found that the phase of the transformed data is a good indicator for identifying an elution peak. Thus, a "phase" method in accordance with embodiments of the present invention transforms at least portions of extracted ion chromatograms or portions of the chromatogram representing raw data from the time domain to the frequency domain. This transformation is beneficial in that it separates the signal of interest at low frequencies from the noise and signal instabilities at high frequency. The signal and corresponding data at low frequencies is of greater interest because masses of interest in the sample will correspond to low frequency components in the chromatogram. However, instead of just looking at the abundance of the low frequency signals, it has been found that the phase of these signals is actually more useful. This is especially so because there may be a mass of interest that has a low abundance such that its peak is hidden by noise or background. In particular, the phase of the single cycle component has been found to be an excellent indicator of the current position on the chromatographic peak. Limiting peak selection to a narrow window of phases allows for triggering near the apex of chromatographic peaks while simultaneously reducing random peak selection by greater than about sixty-five percent.

To reiterate, it is to be appreciated that a beneficial processing technique of the present invention is a combination of the two methods discussed above, wherein the first method provides the noise filtering for a baseline set of m/z of interest while the second method provides the apex detection of a subset of the provided for baseline m/z of interest. This is because the first method used by itself utilizes a simple apex detection method by looking for a decrease in abundance. This simple apex method may erroneously identify a shoulder as an apex. The second method, on the other hand, used by itself, uses a simple intensity threshold which may erroneously identify a continuously eluting background ion. However, by using the correlation method to provide a weighted mass spectrum and then by providing a correlated set of m/z of interest enables the apex detection arrangement of the second method to provide results that are better than either method utilized alone.

Combining the two methods, as described herein, however, does result in an increase of the processing time greater than the processing time for any of the individual methods operating alone. In particular, the first and second methods described above, and in greater detail below, often require about 10 milliseconds each when executed separately using unit resolution bins and a scan width of about 1500 m/z. It is to be appreciated, however, that the combined execution time requires less than the sum of the individual processing steps since the second step of phase analysis needs to be performed only on the bins that pass a correlation processing threshold. In other words, the correlation or first method helps to narrow in on a portion of the chromatogram or the weighted chromatogram of interest such that the phase method need only be performed on a smaller data set, i.e., a subset. Simple estimates indicate that the combined method increases the processing time by less than about twenty-five percent. Thus, a twenty-five percent or less increase can result in a processing time increase from about 10 milliseconds to less than about 12.5 milliseconds.

Accordingly, utilizing such combined methods improves the ability to pick peaks with greater accuracy in a data-dependent fashion during a mass spectrometry analysis, such as, but not limited to, a Liquid Chromatography/Mass Spectrometry (LC/MS) experiment.

Specific Description

Turning now to the drawings, FIG. 1A shows a block diagram, generally designated by the reference numeral 10, which illustrates a combination method of a first and a second method of the present invention. In particular, as shown in FIG. 1A, a set of data is acquired at block 2, the first method (i.e., a correlation method) is implemented at block 6, the second method (i.e., a phase method) is implemented at block 12, and a desired peak is identified and selected, as shown in block 16.

Figure 1B:
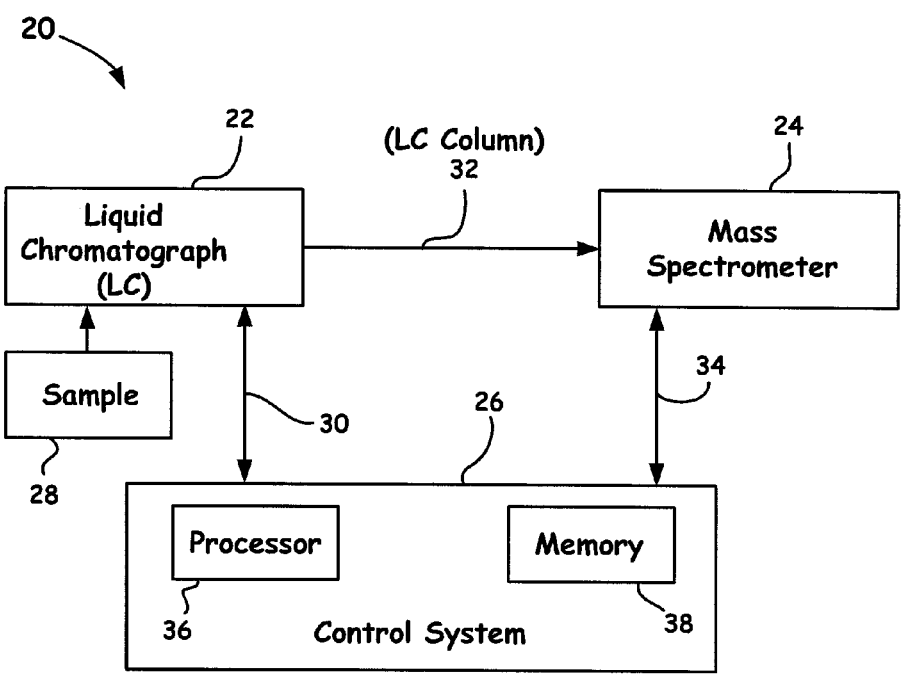
FIG. 1B is a block diagram of a sample processing apparatus that embodies aspects of the present invention.

FIG. 1B shows a simple block diagram of an apparatus, generally designated by the reference numeral 20 that incorporates the general aspects shown in FIG. 1A. Such an apparatus 20 generally includes a liquid chromatograph 22, a mass spectrometer 24, and a controller or control system 26. The liquid chromatograph 22 often is a known type of device, as understood by those of ordinary skill in the art, and thus can be any of a number of commercially-available devices. The liquid chromatograph 22 is designed to receive a sample 28 of a material to be analyzed so that particles of that material, i.e., analytes, can be produced. In particular, the liquid chromatograph 22 outputs analytes (not shown) that are atoms or molecules of the sample 28. The resultant analytes produced by the liquid chromatograph 22 are delivered to the mass spectrometer 24 through a liquid chromatograph (LC) column 32 of a known type, such as, for example, a plastic column, a glass column (e.g., fused silica capillary tube) or a high-performance (HPLC) stainless steel tube.

In an example disclosed embodiment herein, the utilized mass spectrometer 24, while not detailed in the present application, can be arranged from commercially-available devices known and understood by those of ordinary skill in the art, such as, but not limited to, a triple quadrupole, a quadrupole time-of-flight (q-TOF), an ion trap, an ion trap-FT, or an ion trap-Orbitrap. Such compatible mass spectrometers 24 can be configured to perform tandem mass spectrometry, which involves two (e.g., mass spectrometry/mass spectrometry (MS/MS), or more successive stages of mass analysis with a collision or reaction process often occurring between each stage of mass analysis to enhance the ability to determine or identify species or compounds of interest from the sample 28.

In a data-dependent approach of the present invention, using for example, an MS/MS configuration, analytes from the Liquid Chromatograph (LC) column 32 can be processed in the first stage of mass spectrometry in order to identify mass spectral peaks and when a mass spectral peak is identified, the analytes associated with the identified peak(s) are subjected to further evaluation in the second stage of analysis.

The control system 26, shown operatively coupled in FIG. 1B to the liquid chromatograph 22 and the mass spectrometer 24 (note: coupling denoted by reference numerals 30 and 34 respectively), often includes a processor 36, e.g., a microprocessor, and a machine readable medium (a form that can be accessed by an automated sensing device) or memory 38. The memory 38 collectively represents two or more different types of memory, such as, for example, a read only memory (ROM) that can store static data and a program executed by the processor 26 in addition to random access memory (RAM) that is used by the processor 26 to store data that changes dynamically during program execution. While such an arrangement is beneficial in the present invention, the processor 26 and the memory 38 can optionally be implemented as respective portions of a known device that is commonly referred to as a microcontroller.

As stated above, during, for example, tandem mass spectrometry, data from a first stage of mass spectrometry can be monitored to identify mass spectral peaks, and the identification of a mass spectral peak can trigger a second stage of mass spectrometry with respect to analytes that correspond to the peak. Pre-existing techniques for identifying a mass spectral peak have been generally adequate for their intended purposes, but have not been entirely satisfactory in all respects. The apparatus 20, as shown in FIG. 1B, however, takes a different approach to the identification of mass spectral peaks.

Specifically, in describing the coupled method embodiment of the present invention, the first method of analyzing data from a mass spectrometer for a data-dependent acquisition in real-time comprises first taking a series of mass spectral scans of a sample that has eluted from the liquid chromatography (LC) column 32, as shown in FIG. 1B. After eluting from the (LC) column 32, the sample may be ionized by electrospray ionization to put the liquid sample into an ionized gas phase. It is to be noted that while such ionization means are beneficial, other ionization methods may alternately be used, such as, atmospheric pressure chemical ionization, particle beam ionization, and thermospray ionization. After the sample is ionized, the ionized sample can be steered into an ion trap by using electrodynamic and electrostatic forces as known and understood by those of ordinary skill in the art. In an exemplary embodiment, the ion trap is the mass analyzer of the mass spectrometer 24 shown in FIG. 1B.

The amount of ionized sample within the ion trap can be manipulated for each mass spectrum scan by using automatic gain control (AGC) (see for example, U.S. Pat. No. 5,107,109 titled "Method of Increasing The Dynamic Range And Sensitivity Of A Quadrupole Ion Trap Mass Spectrometer" by Stafford et al., and U.S. Pat. No. 5,572,022 titled "Method And Apparatus of Increasing Dynamic Range And Sensitivity Of A Mass Spectrometer" by Schwartz et al., the disclosures of which are herein incorporated by reference in their entirety.

In general, automatic gain control is a method whereby the rate of ion flow into the trap is measured by a prescan to determine the amount of time to fill the ion trap to contain the same amount of ions before each mass spectral microscan. Several mass spectral microscans may be taken before being averaged into a single mass spectral scan. The frequency at which the average mass spectral scan is formed is very dependent on the specific instrument type and the operating mode. Typically, instruments may take one scan per second, although there are some that are capable of up to 100 scans per second. The number of microscans acquired is user selectable. A standard Thermo Finnigan ion trap scans the full mass range 5-6 times per second, with most users operating with a single microscan. The choice of the number of microscans determines a trade-off between speed and spectral quality, i.e., the fewer the number of scans, the faster the speed, the greater the number of scans, the higher the spectral quality.

It is to be appreciated that while a tandem mass spectrometer with a single analyzer (known as tandem in time) is a beneficial arrangement with the present invention, other single stage analyzer systems capable of tandem mass spectrometry are also within the scope and spirit of the present invention, such as, for example, a linear ion trap (LIT), ion cyclotron resonance (ICR), an orbitrap or a Fourier Transform Mass Spectrometer (FTMS).

Moreover, the embodiments of the present invention can also be utilized in a tandem mass spectrometer with more than one analyzer (known as tandem in space.) For example, one mass analyzer can isolate one precursor from many precursors entering a mass analyzer, after which the isolated precursor is collided with a gas within a collision cell causing fragmentation of the isolated precursor. A second mass analyzer then catalogs the fragments produced from the fragmented isolated precursor. Such a process is called collision-induced dissociation and is used for many experiments in proteomics. Multiple stage mass analyzers are utilized for such applications, such as a Quadrupole/oa-time-of-flight (TOF), LIT-TOF, LIT-orbitrap, Quadrupole-ICR, IT-ICR, LIT-oa-TOF, or a LIT-orbitrap mass analyzer.

Figure 2:
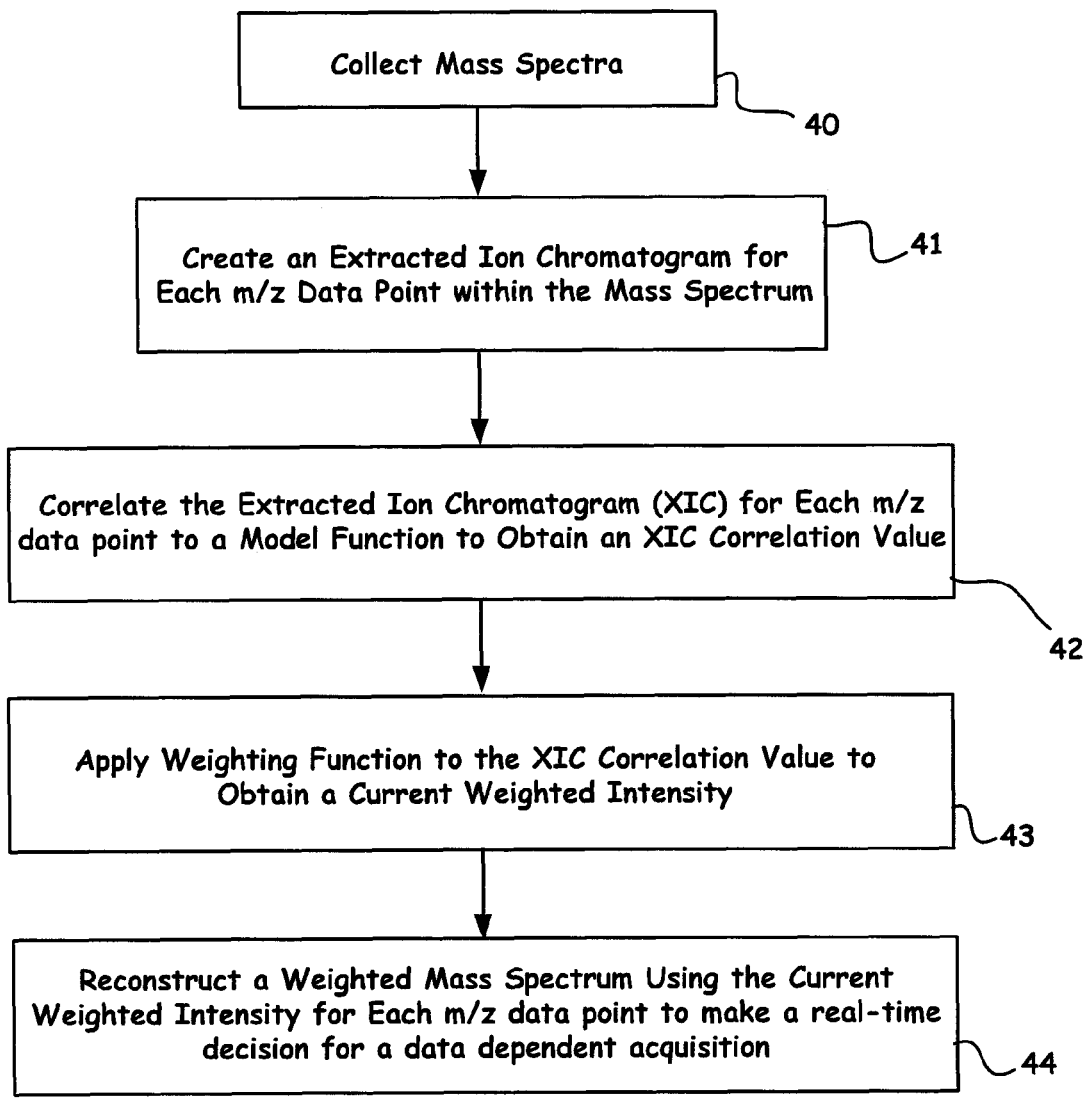
FIG. 2 is a block diagram of the correlation method to determine when to make a data-dependent acquisition.

FIG. 2 shows a block diagram of the steps of the first method, as disclosed herein, applied to one or more mass spectral scans resulting from accumulated precursor ions of an ionized sample within, for example, an ion trap. Once mass spectra, as shown in block 40, have been collected for a predetermined amount of time, an extracted ion chromatogram (XIC) is created, as shown in block 41, for each m/z data point within the mass spectrum. The optimal duration of the predetermined amount of time over which the mass spectra are collected to create such an XIC is dependent on the width of peaks eluting from the chromatograph. In a beneficial embodiment, the predetermined amount of time can be fixed or automatically adjusted based upon observed chromatographic peak widths, such as, for example, between one-half chromatographic peak widths and three chromatographic peak widths, as measured at half maximum height of the collected chromatographic peaks. To minimize processing time, two or more m/z points, or m/z points falling within defined ranges, can be combined before creating each XIC.

FIG. 3A illustrates an example of five mass spectra taken (corresponding to block 40 of FIG. 2) at different times (obtained at predetermined time frames $t_1, t_2, t_3, t_4,$ and $t_5$), which for purposes of explanation contain only three m/z data points a, b, and c. In each of the mass spectra scans illustrated in FIG. 3A, the ion counts are plotted on the y-axis and the m/z (mass to charge ratio) data points are plotted on the x-axis. The m/z data points are a measure of the mass (m) divided by charge (z) of each of the ions detected by, for example, a mass spectrometer having contents of an ion trap. The m/z data points used for processing may be raw data or a copy of the raw data. Using a temporary copy of the raw data may allow for enhanced data-dependent performance without actually altering the data that is returned to the data system and stored in the memory of the controller 26, as shown in FIG. 1B.

The number of mass spectra used to form the extracted ion chromatograms (as implemented in block 41, as shown in FIG. 2) and the number of m/z data points within the mass spectra may vary. The number of mass spectra used to form the extracted ion chromatograms may be within the approximate range of 3 and 20, and the number of m/z data points may be up to about 1,000,000 in a mass spectrum, often in the range of about 5,000 up to about 1,000,000 in a mass spectrum. The wide range of m/z data points that may be collected is due to the variation among different instruments. For example, an ion trap instrument may acquire up to about 15,000 data points and a Fourier transform instrument may acquire up to about 1,000,000 data points.

FIG. 3B illustrates extracted ion chromatograms created for each of the m/z data points (a, b, and c) within the mass spectra of FIG. 3A. The extracted ion chromatogram for each of the m/z data points is then correlated to a model function, such as, but not limited to, a monotonically increasing function, or a gaussian function, to obtain a XIC correlation value, as shown at block 42 of FIG. 2. The model function is a function (a set of time vs. intensity pairs) that matches the expected elution profile of an analyte from a chromatograph. The gaussian function works well for correlation because the chromatographic peaks often have a gaussian shape, but any monotonically increasing function may be used. Other monotonically increasing functions that may be used include, but are not limited to, a Lorentzian function or a linear function. Using a gaussian function in the present example, the XIC correlation value r obtained for the m/z data point c at time point $t_5$, as shown in the bottom left portion of FIG. 3B, is approximately +1 because the XIC for c matches the front half of a gaussian peak. The correlation value r is a measure of how closely the XIC correlates to the first half of a gaussian function or a monotonically increasing function. The XIC correlation value may be any value between −1 and +1. A weighting function is then applied (as shown in block 43 of FIG. 2) to the most recent value of the XIC to obtain a current weighted intensity.

FIG. 3C illustrates such weighted extracted ion chromatograms for the m/z data points a, b, and c, as shown in FIG. 3A. From such example weighted chromatograms, the current weighted intensity for m/z data point a is approximately 0 because the XIC for a is neither increasing nor decreasing. The current weighted intensity for the m/z data point b is negative because the XIC for b is decreasing and the current weighted intensity for the m/z data point c is positive because the XIC for c is increasing The weighting function provides a scaling factor to the raw intensities to reflect how well the XIC represents the expected elution profile. The weighting function may be the product of the XIC correlation value and the most recent time point, the product of a square of the XIC correlation value (while maintaining initial sign) and the most recent time point, or the most recent time point raised to the power of an XIC correlation value. The weighting function serves to emphasize the mass spectral peaks that occur at the actual apex of the chromatographic peak and to also prevent triggering on a tail of a chromatographic peak. This is because once the apex of a chromatographic peak has been passed, the XIC correlation value will be negative.

The weighting function also serves to improve the signal-to-noise in real-time because when the XIC correlation values are near zero, then it is likely that signal is primarily noise. The low intensity peaks may be picked out by this process even when eluting at the same time as a peak of much higher intensity or as a shoulder of another peak. With this method, it is also possible to differentiate eluting peaks from one another when there are many overlapping peaks eluting at the same time and to identify peaks that are much smaller in comparison to other peaks eluting at the same time. This is because the intensity of each m/z data point is independently monitored over time, so even a peak hidden beneath another peak or within noise may be reliably identified. In this way, the correlation method may be used for identifying a baseline of m/z values, e.g., a set of identified ions. That is, identifying a set of ions may include fitting an extracted ion chromatogram taken from the mass spectrum to a function that approximates the front half of a chromatographic peak in preparation of identifying a subset of ions by the second method.

As an example embodiment, a threshold value may be applied to the XIC correlation values to eliminate values below a certain threshold value. For example, the threshold value may be used to de-emphasize a very strong background peak that is not eluting (i.e., it is at a constant level) but may occasionally have a weak correlation, e.g., a correlation of approximately 0.1. The weighted intensity for this very strong background peak may still result in a strong signal. Restricting the correlation value to something such as greater than about 0.5 places a stronger emphasis on the XIC elution profile than on the very strong background peak. Additionally, a threshold value may be used because it is mathematically easier and faster to be able to disregard all of the values below the threshold value.

Although the above indicates that the correlation coefficient method is the technique used to compare the similarity between the XIC data points and the model function, to provide a value that represents how similar they are, the use of the correlation technique is only one aspect of the invention. Other techniques or methods of determining how well the XIC data points fit the model function may also be utilized to accomplish this aim. In the present application, the term "correlation" is intended to cover such alternative techniques.

Turning back to FIG. 2, at block 44, a weighted mass spectrum is then reconstructed using the current weighted intensities for each m/z data point to make a real-time decision for the data-dependent acquisition.

FIG. 3D illustrates such a weighted mass spectrum based on XIC correlation values of the extracted ion chromatograms of FIGS. 3B and 3C. The current weighted intensities for each of the different m/z data points within the reconstructed weighted mass spectrum give an indication of whether the precursor ions from which the m/z data points are derived are increasing, constant, or decreasing in intensity and therefore whether a chromatographic elution peak of the precursor ions exists and whether it is approaching or has already been passed. Whether the chromatographic elution peak is approaching or has already been passed is valuable information for determining when to make a data-dependent acquisition. The data-dependent acquisition may be, for example, the performance of tandem mass spectrometry, the collection of a particular isolated compound eluted from the liquid chromatography column, a diversion to a nuclear magnetic resonance (NMR) analysis, or the spotting of the compound onto a matrix assisted laser desorption and ionization (MALDI) plate.

Figure 4:
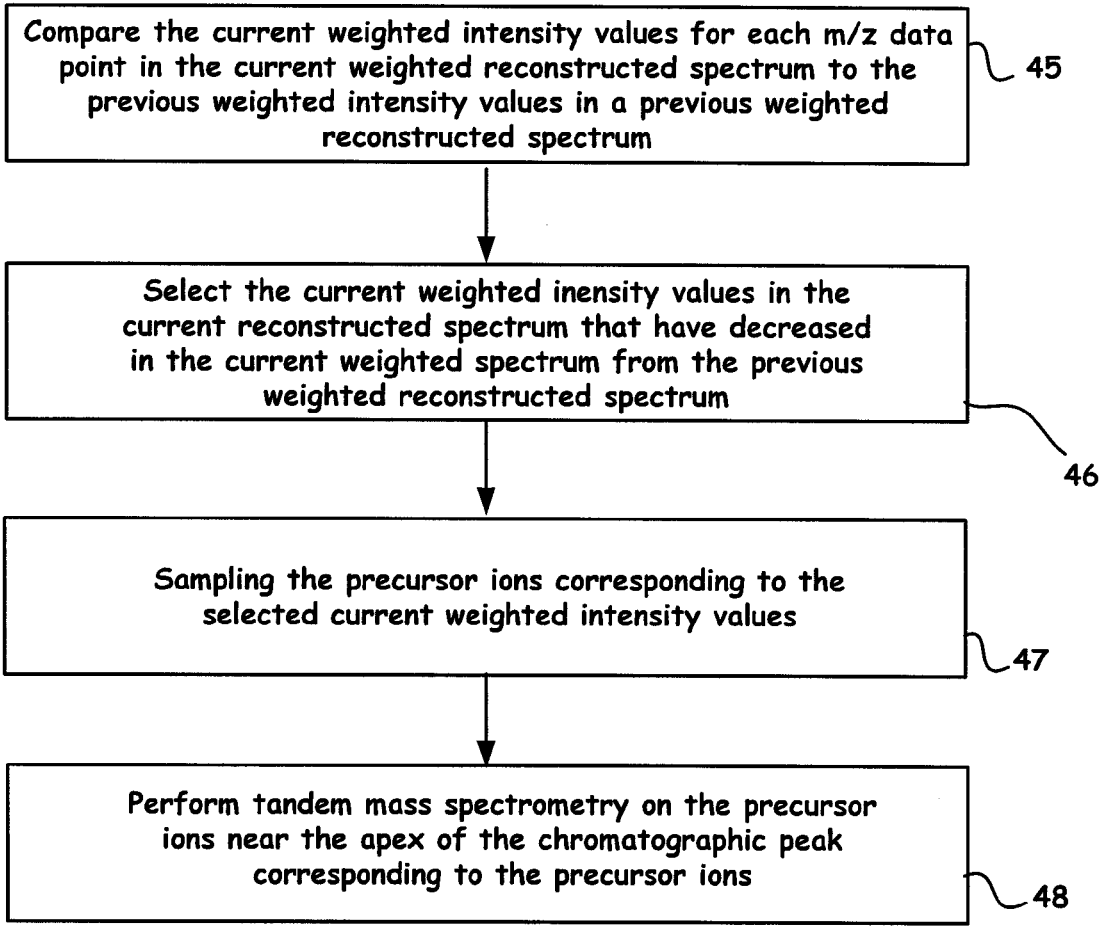
FIG. 4 is a block diagram of methods of selecting mass spectral m/z data points near the apex of the chromatographic peak for tandem mass spectrometry.

FIG. 4 shows a flow chart illustrating a process capable of performing data-dependent acquisition near the apex of a chromatographic peak. In such a process, the method of analyzing data from a mass spectrometer for data-dependent acquisition is expanded upon after reconstructing the weighted mass spectrum, for example, the weighted mass spectrum shown in FIG. 3D. As shown in FIG. 4, at block 45, the weighted intensity for each m/z data point in the current weighted mass spectrum, for example, the weighted mass spectrum shown of FIG. 3D, is compared to the weighted intensity for each m/z data point in a previous weighted mass spectrum.

At block 46, an m/z data point (precursor ion) can be selected if its weighted intensity has decreased in the current weighted mass spectrum from the previous weighted mass spectrum. In the embodiment where tandem mass spectrometry is performed, the precursor ions corresponding to the selected weighted intensities is sampled at block 47 and tandem mass spectrometry is performed on the precursor ion near the apex of the chromatographic peak containing the precursor ion at block 48.

Returning to the discussion involving FIG. 4, it is to be noted that a simple decrease in the weighted intensity of a particular m/z in the current weighted mass spectrum as compared to the previous weighted mass spectrum may not always accurately identify the highest apex, such as when the decrease in intensity corresponds to a shoulder in the mass spectrum.

Accordingly, another beneficial technique for determining a triggering time and of which is beneficially combined with the correlation method discussed above, is set forth below. To illustrate principles of the present invention, the discussion that follows assumes that the apparatus 20, as shown in FIG. 1B, is being utilized to determine whether the sample 28 is a compound having a particular mass-to-charge ratio (m/z) that coincides with an apex of the analyte of interest in the mass spectrum.

In a method of operation, data from the first stage of mass spectrometry is supplied from the mass spectrometer 24 to the control system 26 either without the application of the correlation method or after application of the correlation method so as provide a set of m/z data of interest. The control system 26 uses this data to generate an extracted ion chromatogram (XIC) for the particular mass-to-charge ratio of interest, as has been described above. Generally, suitable techniques for generating an XIC are well-known in the art, and are therefore not further explained in detail here.

Figure 5:
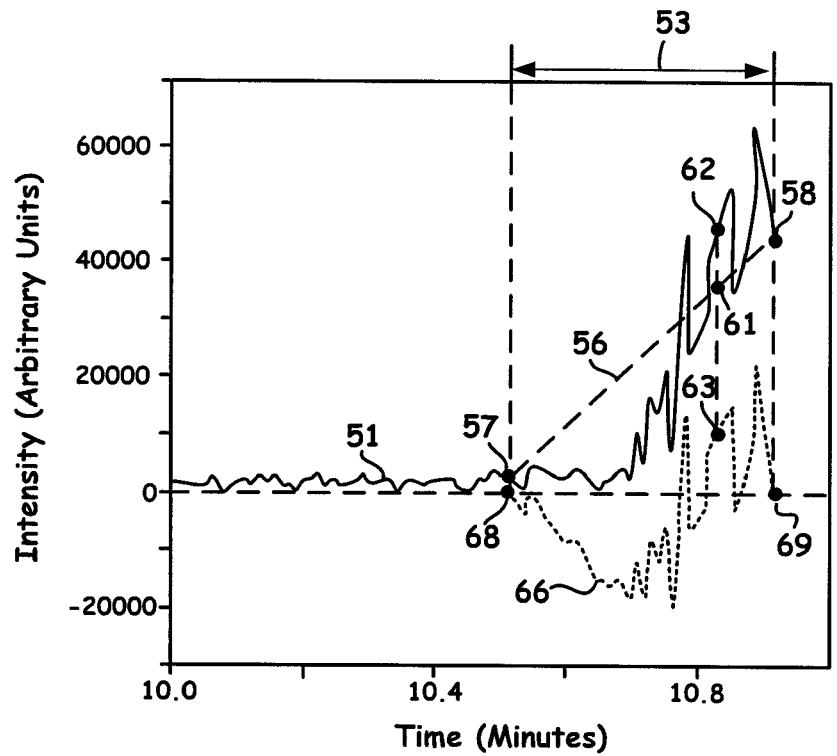
FIG. 5 is a graph showing a curve that is part of an extracted ion chromatogram (XIC) for a selected mass-to-charge ratio, and showing a further curve representing a portion of the XIC curve that has been rotated in preparation for transformation from the time domain to the frequency domain.

FIG. 5 shows a plot having a curve 51 that is part of an XIC for a desired mass-to-charge ratio that is the focus of the present example. As illustrated in FIG. 5, the horizontal axis represents time in minutes, and the vertical axis represents ion counts, in arbitrary units. According to an example aspect of the present invention, a portion of the data from the XIC curve 51 is capable of being converted from the time domain into the frequency domain. Reference numeral 53 (denoted with a double arrow and dashed lines) designates a sliding window that is designed to end with the most recently acquired data with a time window selected to have a length that is approximately equal to the expected width of a chosen elution peak, as measured at the base of such an elution peak.

With respect to transformation methods, the present invention is designed to use any suitable means, such as, but not limited to, a fast Fourier transform method, a wavelet transform method, a Hadamard transform method, a Hilbert transform method, or a Laplace transform method to convert data from the time domain to the frequency domain. Often however, the present invention utilizes a discrete Fourier transform (DFT) method to do such a conversion. A problem can exist, however, if the data being converted using any of the desired methods discussed above, has starting and ending points with different values, then the transformation can distribute power into the frequency domain spectrum, which is undesirable. Therefore, before effecting a conversion from the time domain to the frequency domain, the data to be transformed is first adjusted or "rotated".

In particular, as shown in FIG. 5, assume that an imaginary line 56 is drawn from the starting point 57 to the ending point 58 of a selected data within the sliding window 53, up to and including the most recently acquired point. Then, within the sliding window 53, the value of each point on the line 56 is subtracted from the corresponding point on the curve 51. For example, the value at point 61 on the line 56 is subtracted from the value at the corresponding point 62 on the XIC curve 51, thereby yielding a value indicated at point 63. This procedure yields rotated data, which is represented in FIG. 5 by the curve 66 (now shown as a dashed curve). As shown in FIG. 5, curve 66 now has starting and ending points 68 and 69 that have the same value and are both on the horizontal axis. Next, the rotated XIC data represented by the curve 66 is transformed from the time domain into the frequency domain, often by using standard DFT processing techniques.

Figure 6:
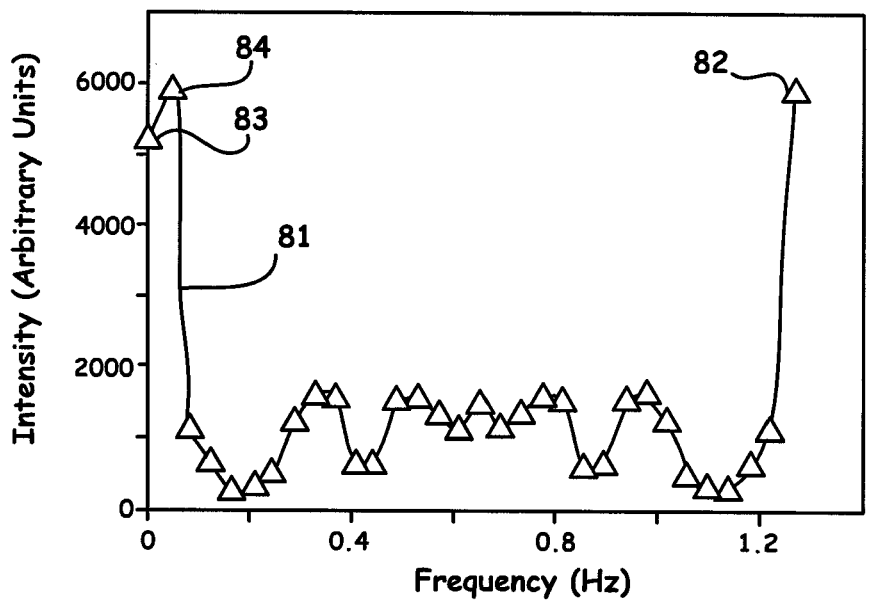
FIG. 6 is a graph showing a curve that represents the magnitude mode frequency domain data obtained by taking rotated time domain data and transforming it into the frequency domain.

FIG. 6 shows a graph having a curve 81 that represents the magnitude mode frequency domain data obtained by taking the time domain data from the curve 66 of FIG. 5 and transforming it into the frequency domain. In the frequency domain, high and low frequency components can be separately identified. In the illustrated example, the source is unstable, as reflected by a relatively large magnitude at 82 for the highest-frequency component. For purposes of the disclosed technique, the component of primary interest is a low-frequency component. The lowest or zero-frequency component, represented by the point 83, is just a measure of the average offset of the data, and can be ignored. The next-lowest component, represented by the point 84, is the "single cycle" frequency. This represents a signal that rotates through one complete cycle over the duration of the transformed time-domain data. This frequency is of primary interest for characterizing and identifying a chromatographic peak. Similarly, the raw data may be transformed from the time domain into the frequency domain. In either case, the frequency domain data includes information about the phase of the single-cycle frequency. Conceptually, a sine or cosine curve can be fitted to the frequency domain data for the single-cycle frequency. The phase of the single-cycle frequency is the phase of the point on the fitted sine or cosine curve that corresponds to the starting point of the single-cycle frequency data.

Figure 7:
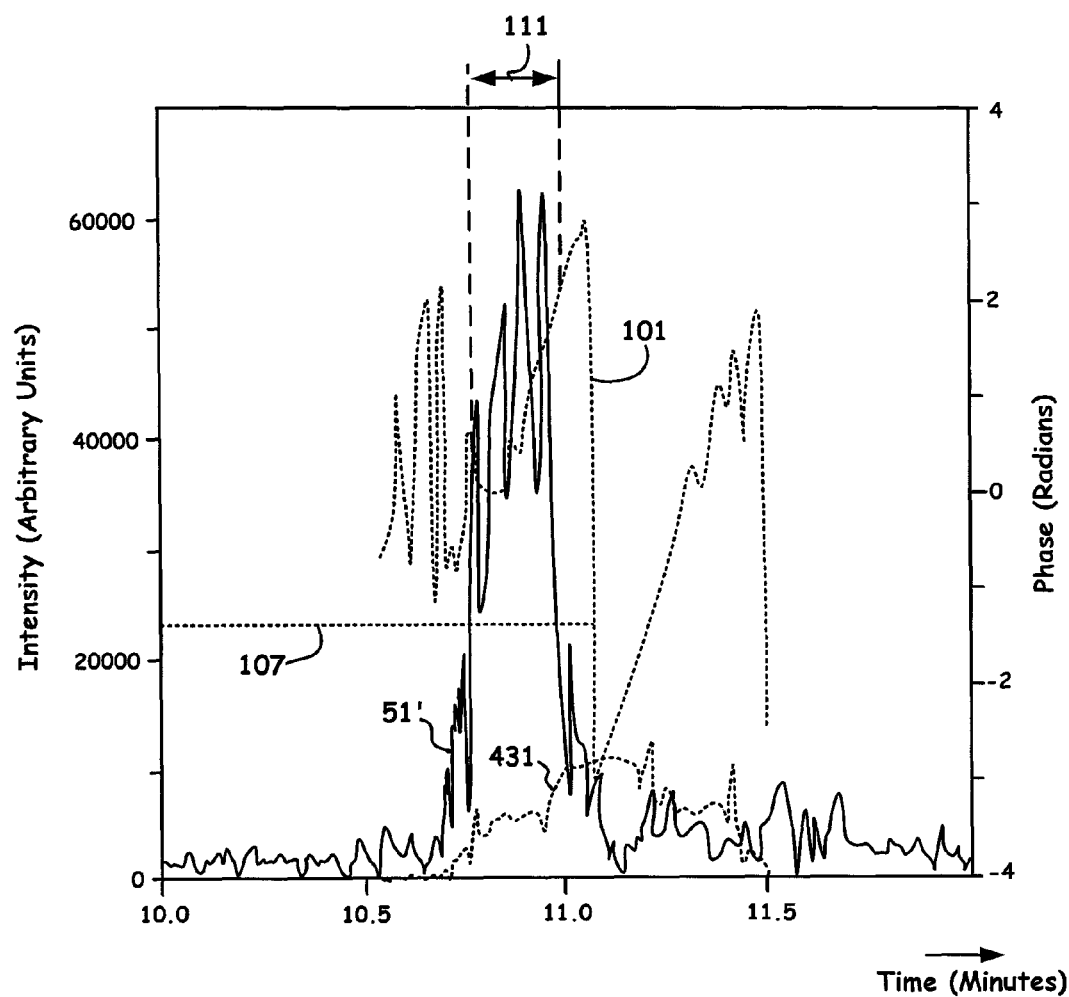
FIG. 7 is a graph showing more of the XIC curve of FIG. 5, showing a further curve representing the magnitude of a single-cycle component of the frequency data in FIG. 6, and showing a phase curve that represents the variation over time of the phase (in radians) of the single-cycle frequency component.

FIG. 7 shows a graph re-illustrating curve 51, as shown in FIG. 5. In particular, FIG. 5 shows only the left portion of the curve, now denoted by the reference numeral 51' in FIG. 7. As discussed in association with FIG. 5, the curve 51' of FIG. 7, shown as a solid line, is the XIC for the particular mass-to-charge ratio of interest, and represents time-domain data. FIG. 7 also depicts a further curve 101 (shown as a dashed line) that represents the variation over time of the phase (in radians) of the single-cycle frequency corresponding to the point 84 in FIG. 6. With reference to the vertical axis on the right side of FIG. 7, the phase varies between approximately $\pi(3.1416)$ and $-\pi(-3.1416)$. Although the curve 51' in FIG. 7 represents time domain data, the curve 101 represents frequency domain data. The curve 51' shows there is a chromatographic peak at a time of approximately 10.9 minutes, and the curve 101 shows that, at this point in time, the phase has a value of approximately $\pi/2$.

With reference to the curve 101, it is noted that the phase data is very noisy at the start of the peak, or in other words before a time of approximately 10.7 minutes. This is primarily because a low-frequency component is of low magnitude. With significant magnitude, the phase varies smoothly from $-\pi$ to $\pi$. At 11.1 minutes, there is an apparent discontinuity in the phase 101, but this is actually the phase wrapping around from $\pi$ back down to $-\pi$, rather than a true discontinuity. This phase data can be used to help identify a chromatographic peak. In particular, if the phase has a current value that is within a certain window, for example between about $\pi/4$ and about $3\pi/4$, then the selected mass-to-charge ratio is eligible for data-dependent selection.

Turning back to FIG. 7, it is noted that there are several different points in time where the phase falls within the window of $\pi/4$ to $3\pi/4$. Consequently, to accurately identify a chromatographic peak, a further selection criterion is used. To illustrate such a criterion, FIG. 7 shows a user-selected threshold 107 (denoted with a dashed line). In FIG. 7, the threshold 107 corresponds to an intensity of approximately 23,000. However, this is purely by way of example, and a user can select the threshold 107 to be either higher or lower. If the curve 51' is below the threshold, then the phase 101 is ignored. In other words, if the curve 51' is below the threshold 107, then the system does not need to prepare the rotated data (curve 66 as shown in FIG. 5), and does not need to convert this rotated data from the time domain to the frequency domain to obtain phase data. On the other hand, when the curve 51' is above the threshold 107, then the system prepares the rotated data (curve 66 as shown in FIG. 5), converts this rotated data from the time domain to the frequency domain to obtain phase data, and then evaluates the phase data. Thus, in FIG. 7, the portion of the phase data 101 that is actually calculated and taken into account is the portion within a time window 111 when the curve 51' is above the threshold 107. This has the beneficial aspect that the processor (26 as shown in FIG. 1B) does not waste time carrying out complex calculations of data that will be ignored.

Proper selection of the length of the sliding time window (reference numeral 53, as shown in FIG. 5) can improve the accuracy with which the foregoing technique identifies an elution peak. In the disclosed embodiment, the sliding window 53, as shown in FIG. 5, as discussed above, is selected to have a length that is approximately equal to the expected width of the elution peak, as measured at the base of the elution peak.

Figure 8:
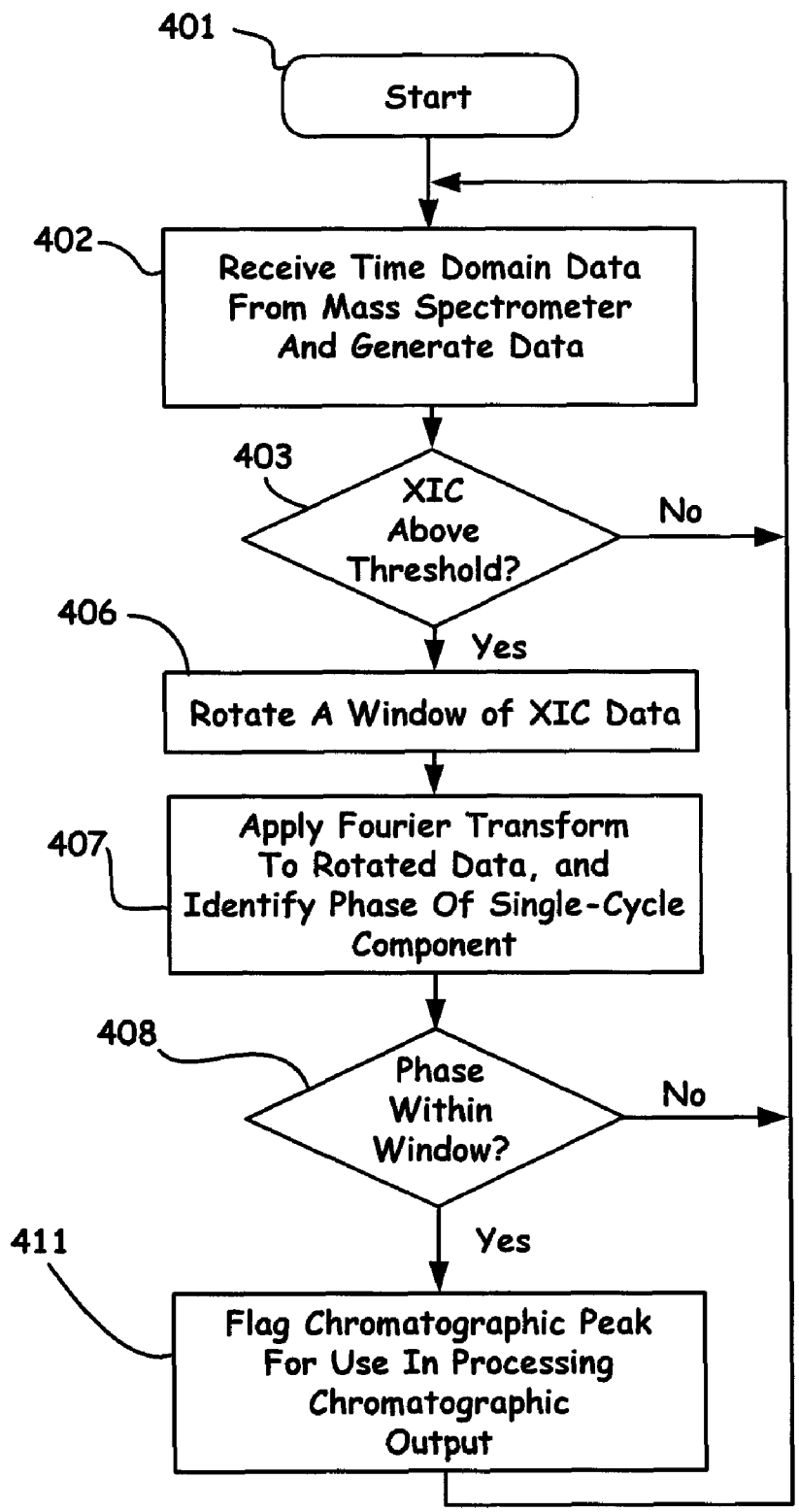
FIG. 8 is a flowchart showing a sequence of operations carried out by a processor of the present invention.

FIG. 8 is a flowchart that summarizes the technique described above. In particular, the processor 36, as shown in FIG. 1B, begins in block 401, and proceeds to block 402, where time domain data from the mass spectrometer 24, as shown in FIG. 1B, is used to generate XIC data. Control then proceeds to block 403, where a determination is made as to whether the current value of the XIC data is above a threshold. If not, then control returns to block 402, in order to continue to receive time domain data and calculate further XIC data for the mass-to-charge ratio of interest, or for a range of mass-to-charge ratios of interest. On the other hand, if it is determined in block 403, as shown in FIG. 8, that the current XIC data is above the threshold, then control proceeds to block 406, where a window of XIC data is rotated in the manner discussed earlier, in order to obtain rotated data such as that shown by reference numeral 66, as shown in FIG. 5. Control then proceeds to block 407, where a discrete Fourier transform is used to transform the rotated data from the time domain into the frequency domain, and to then identify the phase of a single-cycle component of the rotated data. In the case of the example discussed above, this corresponds to a point on the phase curve 101 in FIG. 7.

Control then proceeds to block 408, where a determination is made on whether the current phase value is within a selected window or range, such as $\pi/4$ to $3\pi/4$ radians, or 0 to 2 radians. If not, then control returns to block 402. Otherwise, control proceeds to block 411, where the system flags the identification of a chromatographic peak, so that this can be subsequently used for processing material of a chromatographic output. For example, the accurate identification of a chromatographic peak can be used to carry out a second mass analysis in tandem mass spectrometry. Alternatively, the accurate identification of a chromatographic peak can be saved, and then used to carry out mass spectrometry in a later scan of the same sample.

In comparison to existing techniques, the technique(s) disclosed herein is beneficial for identifying the apex of a chromatographic peak, and is beneficial for eliminating problems caused by source instability. The disclosed transformation technique(s) to enable the phase information to be derived often, as discussed above, uses a discrete Fourier transform (DFT). Alternatively, however, the rotated data can be converted from the time domain to the frequency domain using any other suitable type of transform, including a fast Fourier transform (FFT). In the case of an FFT, the FFT expects input data in the form of a number of data points that are a power of two. Since the sliding window 53, as shown in FIG. 5, has a length that is selected based on a time criteria, rather than the amount of data, the number of data points associated with the sliding window is typically not automatically a power of two. In such a case, the time-domain data associated with the sliding window can be supplemented with "dummy" points up to the next power of two, where the dummy points represent a set of values that can maintain continuity between the beginning and end of the rotated data. In the case of an FFT, a further consideration is that the FFT normally expects data points that are spaced equally in time. The disclosed technique produces data points that may not be spaced equally in time. But in most cases, the unequal spacing of data points do not have a significant effect on the results.

The foregoing transformation discussion can thus often include two selection criteria for determining if the data is eligible for data dependent selection, e.g., whether the current value of XIC data is above a threshold, and then determining whether the current value of the phase for a single-cycle frequency is within a selected phase window. However, it is also possible to use other criteria, either in addition to these criteria, or in place of one or both of these two criteria. One such criterion is monitoring the trend of the phase information, for example by looking for three points in a row where the phase is progressively increasing. As another alternative, the technique described above contemplates that the real and imaginary components produced by the Fourier transform be combined. However, as another example arrangement, one can utilize either the real component or the imaginary component, without first combining the two.

Still another alternative selection criterion can be based on the magnitude of the single-cycle frequency component. For example, in FIG. 7, reference numeral 431 designates a curve representing part of the frequency domain data obtained with the Fourier transform. More specifically, the curve 431 represents the variation over time of the magnitude of the single-cycle component in the frequency domain. Instead of comparing the XIC curve 51' to the threshold 107 in order to determine whether or not to consider phase data, the magnitude of the curve 431, as shown in FIG. 7, can be compared to an appropriate threshold in order to determine whether or not to consider phase data.

Another example selection criterion involves use of the rotation angle of the rotated data. For example, with reference to FIG. 5, if the portion of the XIC curve 51 that is to be rotated has a starting point, as denoted by reference numeral 57, with a value lower than the value of the end point 58, then rotation followed by Fourier transformation is carried out. In contrast, if the starting point 57 had a value higher than the value of the end point 58, then rotation and Fourier transformation is not carried out. This rotation angle criterion can, for example, be used in combination with the above-mentioned phase criterion, and the above-mentioned threshold criterion for the curve 431 as shown in FIG. 7.

Further, as discussed above in association with FIG. 5, the XIC curve 51 is generated using known techniques. These known techniques typically involve "binning" of mass-to-charge ratios detected by the mass spectrometer. For the purpose of the techniques described herein, binning is typically done at unit resolution, i.e., with bin widths of 1 m/z per bin. However, the present invention can be arranged to use wider bins, and such a technique is still effective in spotting eluting peaks despite the frequency data obtained being slightly noisier. But where this noise is tolerated, then initial binning can occur using a wider width such as 5 m/z per bin. Then, any of the wider bins that met all selection criteria can be further analyzed at a higher binning resolution such as 1 m/z per bin, in order to more accurately identify a mass of interest. For instruments with high resolution capabilities, such as FTICR and orbitrap, narrower bins can be used to assist in separating distinct masses. A further factor that can influence bin width is the particular type of sample material 28, as shown in FIG. 1B, that is being analyzed. For example, samples with more complex mixtures might require finer binning than relatively simple samples.

As described above, the first and second method may be combined. For example, once a set of m/z data has been identified such as by a correlation method, narrowing in on a subset of m/z data of interest may include identifying data corresponding to a low frequency portion of the corresponding XIC's. As an alternate arrangement, the combination of the first and second methods may include narrowing in on the subset of m/z data of interest by identifying data corresponding to a single cycle component of the low frequency portion of the XIC's. Selecting data based on this method results in acquiring data at a time corresponding to elution of at least one m/z peak in a subset of data left after initial baseline filtering or thresh-holding.

The identifying of a set of m/z values and the selecting of a subset of m/z values may be executed under instructions stored on a machine-readable medium (e.g., a computer readable medium) coupled to a sample processing apparatus. A computer-readable medium, in accordance with aspects of the present invention, refers to mediums known and understood by those of ordinary skill in the art, which have encoded information provided in a form that can be read (i.e., scanned/sensed) by a machine/computer and interpreted by the machine's/computer's hardware and/or software. When, for example, mass spectra data of a mass spectrum is received by the apparatus disclosed herein, the information embedded in a computer program of the present invention can be utilized, for example, to extract data (e.g., a weighted mass spectrum) from the mass spectral data, which corresponds to a selected set of mass-to-charge ratios. In addition, the information embedded in a computer program of the present invention can be utilized to carry out methods for identification of an elution peak in a manner that includes determining whether phase information in the frequency domain data meets a phase criterion. The computer program may also identify, as a function of the frequency domain data, one or more elution peaks of m/z of interest. The computer program, when executed, may carry out the extraction in a manner so that the resulting data represents a period of time approximately equal to the expected width of the elution peak. The width of the elution peak may be measured in the region of the base thereof for this purpose. When executed, the computer program may also cause processing of material generated from a chromatographic output as a function of an identified elution peak.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention, as defined by the following claims.

The invention claimed is:

1. A method of enabling data-dependent acquisition in a mass spectrometer, comprising:
   obtaining a plurality of mass spectra from a sample;
   selecting from said plurality of mass spectra, a set of eluting m/z peaks of interest from a weighted mass spectrum by way of a correlation technique;
   obtaining phase data resulting from portions of extracted ion chromatographs (XIC) from said selected set of eluting m/z peaks of interests so that a subset of said set of eluting m/z peaks of interest can be identified; and
   triggering off of said identified subset of said eluting m/z peaks of interest based on said obtained phase data so that real-time data is acquired that corresponds to one or more eluting m/z peaks of interest.

2. The method of claim 1, wherein said correlation technique further comprises:

correlating an extracted ion chromatogram taken from said plurality of mass spectra to a function that approximates a chromatographic peak.

3. The method of claim 2, wherein said correlation technique further comprises:
   setting a threshold correlation value so that elution peaks that have a weak correlation are de-emphasized.

4. The method of claim 1, wherein said obtained mass spectra of said sample comprises an elution chromatogram with one or more resultant chromatographic peak widths, wherein an extracted ion chromatogram (XIC) is formed of mass spectra collected for a predetermined time window between one half and three times the width of a predetermined resultant chromatographic peak width as measured at half maximum height.

5. The method of claim 4, wherein said predetermined amount of time window is fixed.

6. The method of claim 1, wherein said obtaining phase data step further comprises:
   identifying data corresponding to a low frequency portion of said set of m/z interest that results from transformation of said identified data from the time domain to the frequency domain.

7. The method of claim 6, wherein said low frequency portion further comprises:
   a single-cycle component of the frequency domain of said subset of m/z interest.

8. The method of claim 7, wherein a selection criterion based on the magnitude of said single-cycle component provides for data dependent eligibility.

9. The method of claim 1, wherein said obtaining phase data step further comprises: determining whether said obtained phase information meets a phase criterion so that raw data or data comprising extracted ion chromatographs (XIC) from said selected set of eluting m/z peaks of interests that are transformed from the time domain to the frequency domain can be eligible for data-dependent selection.

10. The method of claim 9, wherein said phase criterion is between about $\pi/4$ and about $3\pi/4$.

11. The method of claim 1, wherein said obtaining phase data step further comprises, determining whether the trend of phase information progressively increases so that a desired said transformed data can be eligible for data-dependent selection.

12. The method of claim 1, wherein said obtaining phase data step comprises phase information resulting from raw data.

13. A computer readable medium that provides instructions, which when executed on a processor, causes the processor to perform a method of controlling a mass spectrometer, comprising:
   obtaining a plurality of mass spectra from a sample;
   selecting from said plurality of mass spectra, a set of eluting m/z peaks of interest from a weighted mass spectrum by way of a correlation technique;
   obtaining phase data resulting from portions of extracted ion chromatographs (XIC) from said selected set of eluting m/z peaks of interests so that a subset of said set of eluting m/z peaks of interest can be identified; and
   triggering off of said identified subset of said eluting m/z peaks of interest based on said obtained phase data so that real-time data is acquired that corresponds to one or more desired eluting m/z peaks of interest.

14. The computer-readable medium of claim 13, wherein said instructions, when executed, carries out the identification of an elution peak in a manner that further comprises:

determining whether said obtained phase information meets a phase criterion so that raw data or data comprising extracted ion chromatographs (XIC) from said selected set of eluting m/z peaks of interests that are transformed from the time domain to the frequency domain can be eligible for data-dependent selection.

15. The computer-readable medium of claim 14, wherein said set of instructions, when executed, carries out the identification of an elution peak in a manner that comprises:
determining whether the trend of phase information of said obtained phase data progressively increases so that a transformed data from the time domain to the frequency domain can be eligible for data-dependent selection.

16. The computer-readable medium of claim 15, wherein said transformed data comprises a single-cycle component of the frequency domain.

17. The computer-readable medium of claim 16, wherein a selection criterion based on the magnitude of said single-cycle component provides for data dependent eligibility.

18. The computer-readable medium of claim 13, wherein said obtained mass spectra of said sample comprises an elution chromatogram with one or more resultant chromatographic peak widths, wherein an extracted ion chromatogram (XIC) is formed of mass spectra collected for a predetermined time window between one half and three times the width of a predetermined resultant chromatographic peak width as measured at half maximum height.

19. A sample processing apparatus for data-dependent acquisition, comprising:
a mass spectrometer;
a system controller for controlling said mass spectrometer; and
a machine-readable medium coupled to said system controller, said machine-readable medium having a memory that stores a set of instructions that controls data-dependent acquisition by said mass spectrometer; wherein said set of instructions comprises:
obtaining a plurality of mass spectra from a sample;
selecting from said plurality of mass spectra, a set of eluting m/z peaks of interest from a weighted mass spectrum by way of a correlation technique;
obtaining phase data resulting from portions of extracted ion chromatographs (XIC) from said selected set of eluting m/z peaks of interests so that a subset of said set of eluting m/z peaks of interest can be identified; and
triggering off of said identified subset of said eluting m/z peaks of interest based on said obtained phase data so that real-time data is acquired that corresponds to one or more desired eluting m/z peaks of interest.

20. The sample processing apparatus of claim 19, wherein said selecting of said set of eluting m/z peaks of interest further comprises:
extracting an ion chromatogram (XIC) from said mass spectra, wherein said extracted ion chromatogram is correlated to a function that approximates a chromatographic peak.

21. The sample processing apparatus of claim 20, wherein said extracted ion chromatogram (XIC) is formed of mass spectra collected for a predetermined time window between one half and three times the width of a predetermined chromatographic peak width as measured at half maximum height.

22. The sample processing apparatus of claim 19, wherein said identified subset of m/z interest comprises a single-cycle component of the frequency domain of a transformed data of said set of eluting m/z peaks of interest.

23. The sample processing apparatus of claim 22, wherein a selection criterion based on the magnitude of said single-cycle component provides for data dependent eligibility.

24. The sample processing apparatus of claim 19, wherein said identified phase data further comprises a selected phase criterion so that raw data or data comprising extracted ion chromatographs (XIC) from said selected set of eluting m/z peaks of interests that are transformed from the time domain to the frequency domain can be eligible for data-dependent selection.

25. The sample processing apparatus of claim 19, wherein a trend of said obtained phase data is monitored so that desired said transformed data of eluting m/z peaks of interest can be eligible for data-dependent selection.

* * * * *